(12) United States Patent
Tharan et al.

(10) Patent No.: US 11,318,241 B2
(45) Date of Patent: May 3, 2022

(54) SYSTEM AND METHOD FOR WOUND MONITORING

(71) Applicant: Medsix Inc., Boston, MA (US)

(72) Inventors: Nikin Tharan, Boston, MA (US); Indraneil Mukherjee, New York, NY (US); Niloy Choudhury, Newton, MA (US); Max Narovlyansky, Revere, MA (US)

(73) Assignee: Medsix Inc., Boston, MA (US)

( * ) Notice: Subject to any disclaimer, the term of this patent is extended or adjusted under 35 U.S.C. 154(b) by 328 days.

(21) Appl. No.: 16/804,897

(22) Filed: Feb. 28, 2020

(65) Prior Publication Data

US 2020/0306423 A1 Oct. 1, 2020

Related U.S. Application Data (60) Provisional application No. 62/824,700, filed on Mar. 27, 2019, provisional application No. 62/890,236, filed on Aug. 22, 2019.

(51) Int. Cl.
*G08B 23/00* (2006.01)
*A61M 1/00* (2006.01)
(Continued)

(52) U.S. Cl.
CPC ........... *A61M 1/734* (2021.05); *A61B 5/0004* (2013.01); *A61B 5/1032* (2013.01);
(Continued)

(58) Field of Classification Search
CPC ................ A61M 1/734; A61M 1/69; A61M 2205/3303; A61M 2205/3334; A61M 2205/3584; A61M 2205/36; A61M 2205/583; A61M 2205/3306; A61M 2205/3368; A61M 1/70; A61M 1/73;
(Continued)

(56) References Cited

U.S. PATENT DOCUMENTS 7,241,287 B2 * 7/2007 Shehada ............ A61B 5/14539
600/549
7,267,671 B2  9/2007 Shehada
(Continued)

FOREIGN PATENT DOCUMENTS

CN   107024580 A   8/2017
CN   109498854 A   3/2019
(Continued)

*Primary Examiner* — Toan N Pham
(74) *Attorney, Agent, or Firm* — Cesari & McKenna, LLP (57) ABSTRACT

A wound monitoring system including a sensor for detecting color and flow rate of a fluid flowing through a wound drain tubing, a base station for receiving color and flow rate data from the sensor over the one or more networks, for storing the data, and for sending notifications over the one or more networks, and a user device for receiving the notification over the one or more networks. Also disclosed is a wound monitoring system that includes the sensor, the base station, a cloud server, and the user device. The base station receives the data from the sensor and transmits the data over one or more networks to the cloud server. Further disclosed is a wound drain monitoring method that employs the wound monitoring system.

25 Claims, 9 Drawing Sheets

(51) Int. Cl.
*G16H 10/60* (2018.01)
*A61B 5/103* (2006.01)
*A61B 5/145* (2006.01)
*A61B 5/00* (2006.01)

(52) U.S. Cl.
CPC .......... *A61B 5/14507* (2013.01); *A61B 5/742* (2013.01); *A61M 1/69* (2021.05); *G16H 10/60* (2018.01); *A61M 2205/3303* (2013.01); *A61M 2205/3334* (2013.01); *A61M 2205/3584* (2013.01); *A61M 2205/36* (2013.01); *A61M 2205/583* (2013.01)

(58) Field of Classification Search
CPC . A61B 5/0004; A61B 5/1032; A61B 5/14507; A61B 5/742; A61B 5/1455; A61B 5/445; A61B 5/6865; G16H 10/60; G16H 30/40; G16H 40/67
See application file for complete search history.

(56) References Cited

U.S. PATENT DOCUMENTS

| | | | |
|---|---|---|---|
| 7,753,902 | B1 | 7/2010 | Mansour et al. |
| 9,526,816 | B2* | 12/2016 | Toth ................. A61M 1/74 |
| 10,086,117 | B2 | 10/2018 | Locke et al. |
| 10,155,070 | B2 | 12/2018 | Childress et al. |
| 10,207,031 | B2* | 2/2019 | Toth ................. A61B 5/445 |
| 10,258,252 | B1 | 4/2019 | Cudney |
| 10,441,170 | B2 | 10/2019 | Hamilton et al. |
| 10,568,552 | B2 | 2/2020 | Wedekind et al. |
| 2008/0269582 | A1 | 10/2008 | Mansour et al. |
| 2012/0190956 | A1 | 7/2012 | Connolly |
| 2016/0166438 | A1 | 6/2016 | Rovaniemi |
| 2017/0281064 | A1 | 10/2017 | Bayon |
| 2018/0055359 | A1 | 3/2018 | Shamim et al. |
| 2018/0229014 | A1 | 8/2018 | Guirguis |
| 2019/0046102 | A1 | 2/2019 | Kushnir |
| 2019/0060126 | A1 | 2/2019 | Emmons et al. |
| 2019/0142644 | A1 | 5/2019 | Askem et al. |
| 2019/0151156 | A1 | 5/2019 | Kieswetter et al. |
| 2019/0183683 | A1 | 6/2019 | Duesterhoft et al. |
| 2019/0200865 | A1 | 7/2019 | Hwang et al. |
| 2019/0262180 | A1 | 8/2019 | Engel et al. |
| 2019/0282738 | A1 | 9/2019 | Hartwell et al. |
| 2019/0290496 | A1 | 9/2019 | Brownhill et al. |

FOREIGN PATENT DOCUMENTS

| | | |
|---|---|---|
| CN | 109498857 A | 3/2019 |
| CN | 109621065 A | 4/2019 |
| JP | 2009-300337 | 12/2009 |
| WO | WO-2018/156667 A1 | 8/2018 |
| WO | WO-2020/061334 A1 | 3/2020 |

* cited by examiner

SYSTEM AND METHOD FOR WOUND MONITORING

CROSS-REFERENCE TO RELATED APPLICATIONS

This application claims the benefit of U.S. Provisional Application No. 62/824,700, filed on Mar. 27, 2019 and U.S. Provisional Application No. 62/890,236, filed on Aug. 22, 2019. The content of both prior applications is hereby incorporated by reference in its entirety.

BACKGROUND

Wound drainage systems that include a fluid collection bag are installed following surgery to collect and dispose of excess wound fluids as the body heals. In the hospital, the volume of wound fluid is monitored and color is observed each time the collection bag is disposed of and replaced. This typically occurs as often as hourly to twice a day or as infrequently as once per week, depending on the amount of fluid flow and the type of surgery.

A color change in the wound fluid, for example from clear to red, indicates that the patient may be bleeding internally. In another example, if the wound fluid volume increases precipitously, the patient might be bleeding excessively. Typically, these wound fluid changes are observed using a manual process on an intermittent basis. There may be a delay of a few hours in detecting the changes, even under highly supervised situations, such as an intensive care unit.

The expected complications that often arise during post-operative recovery are compounded by delayed detection and reporting. Bleeding or infection, if not detected for several hours or days, can lead to minor, major, and catastrophic events that may require hospital readmission, additional surgeries, and increased patient recovery time.

Furthermore, patients who undergo complex highly risky surgery and are expected to heal slowly are often discharged with the wound drain still in place. They are asked to self-monitor the volume and color of the wound fluid without any assistive tools. These patients often have physical limitations, lack the technical expertise to self-monitor, and typically report an issue only when they are feeling ill, resulting in poor compliance with wound drain monitoring and reporting.

There are approximately 300,000 surgeries annually in the United States alone in which wound drains are inserted. Furthermore, it is estimated that hospital readmissions for surgical site infections cost the US healthcare system an estimated $3-10 billion annually. Early detection of surgical complications, e.g., bleeding and infection, from color and flow monitoring of wound drain fluid would speed recovery times and reduce hospital readmissions, thus reducing patient morbidity and realizing significant cost savings.

A wound monitoring system is needed that can continually monitor wound drain fluid color and flow automatically, thus facilitating early detection of complications during post-operative recovery.

SUMMARY

To meet this need, a wound monitoring system is provided. The system includes (i) a sensor for detecting color and flow rate of a fluid flowing through a wound drain tubing, the sensor including a wireless transmitter for transmitting data for the color and the flow rate over one or more networks to a base station; (ii) a base station for receiving the data over the one or more networks, for storing the data, and for sending notifications over the one or more networks; and (iii) a user device for receiving the notification over the one or more networks.

The base station includes at least one processor configured to compare the data with predefined parameters stored at the base station, to send a notification over the one or more networks to a user device if the predefined parameters are met by the data, and to update an electronic health record (EHR) with the data. The at least one processor of the base station is further configured to analyze the EHR and the data stored at the base station to predict clinical outcomes and to modify the predefined parameters based on the predicted clinical outcomes.

The user device, which can be used for modifying the predefined parameters stored at the base station, is configured to present the notification on a display device of the user device to a user, to accept one or more input commands via a graphical user interface of the user device from the user for modifying the predefined parameters, and to transmit the modified predefined parameters to the base station over the one or more networks.

Another wound monitoring system of the invention also includes a cloud server in addition to the sensor, the base station, and the user device. In this particular system, the base station receives the data from the sensor and transmits the data over one or more networks to the cloud server.

The cloud server includes at least one processor configured to compare the data with predefined parameters stored at the cloud server, to send a notification over the one or more networks if the predefined parameters are met by the data, and to update an EHR with the data. The at least one processor is further configured to analyze the EHR and the data stored at the cloud server to predict clinical outcomes and to modify the predefined parameters based on the predicted clinical outcomes.

In this system, the user device receives the notification over the one or more networks from the cloud server. The user device can modify the predefined parameters stored at the cloud server and is configured to present the notification on a display device of the user device to a user, to accept one or more input commands via a graphical user interface of the user device from the user for modifying the predefined parameters, and to transmit the modified predefined parameters to the cloud server over the one or more networks.

Also provided is a method for monitoring a wound fluid. The method is carried out by (i) affixing a sensor to a wound drain tubing external to a patient, the sensor containing a color detector, a flow detector, and a wireless transmitter for transmitting data for the color and the flow rate over one or more networks to a base station; (ii) programming the base station with parameters for notification related to the data for the color and the flow rate, the notification to be sent to a user device over the one or more networks when the data for the color and the flow rate data meet the parameters indicating one or more of infection, bleeding, and drain blockage; and (iii) activating the base station, wherein the activating causes the base station to periodically update an electronic health record of the patient with the data for the color and the flow rate and continuously compare the data with the parameters. When the parameters are met, the notification is sent to the user device over the one or more networks such that proper medical attention can be provided.

The details of one or more embodiments are set forth in the description and the examples below. Other features, objects, and advantages will be apparent from the detailed description, from the drawings, and also from the appended claims.

BRIEF DESCRIPTION OF THE DRAWINGS

The description below refers to the accompanying drawings, of which.

DETAILED DESCRIPTION

Figure 1:
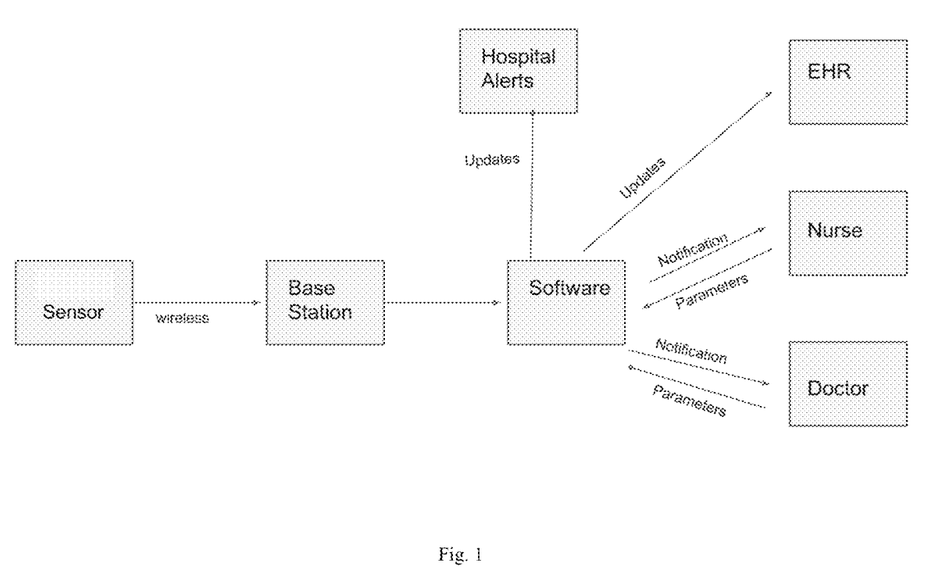
FIG. 1 is a schematic diagram of a wound monitoring system of the invention.
Figure 2A:
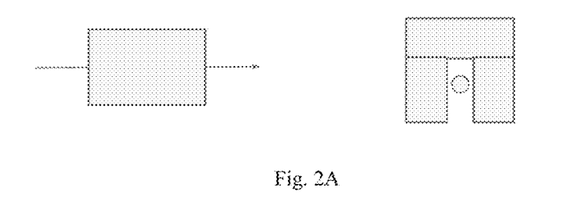
FIG. 2A shows a side view (left) and straight-on view (right) of a particular arrangement of a sensor arranged on a wound drain tubing.
Figure 2B:
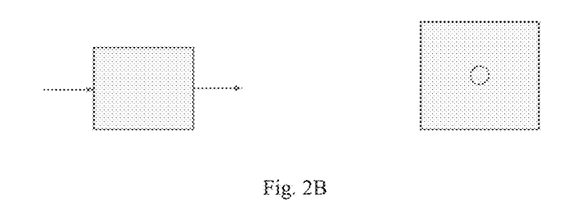
FIG. 2B shows a side view (left) and straight-on view (right) of an alternative arrangement of a sensor arranged on a wound drain tubing.

The wound monitoring system encompassed by the invention is shown schematically in FIG. 1. As mentioned above, the system has a sensor for measuring the color and flow rate of wound fluid. The sensor can be mounted on a length of wound drain tubing by, e.g., clamping it onto the outside of the tubing (see FIG. 2A) and by threading the tubing through the sensor (see FIG. 2B).

Figure 3A:
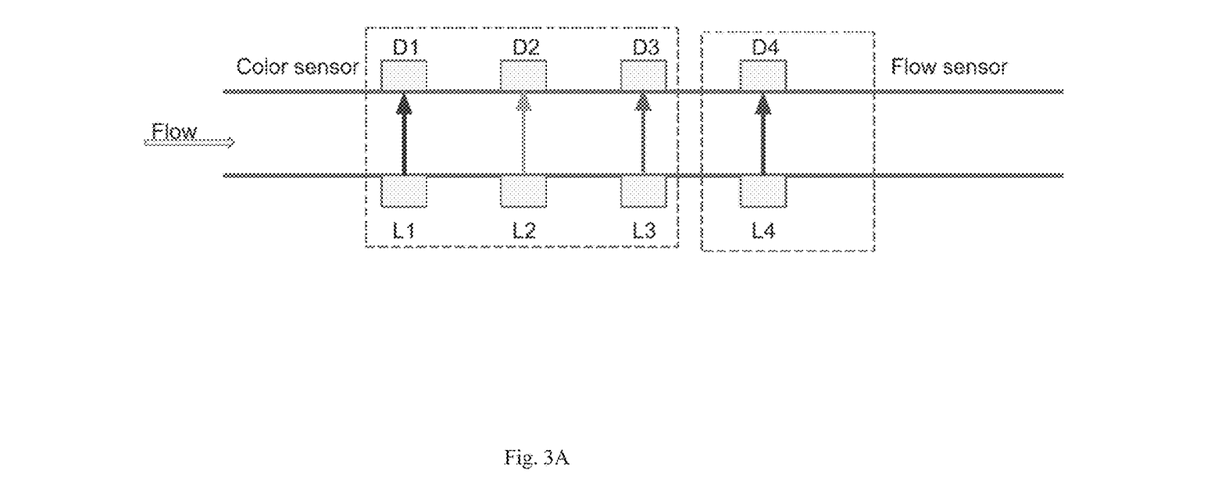
FIG. 3A diagrams the arrangement of color and flow sensors for detecting color and flow rate by transmission: L1, L2, L3, and L4 are blue light source, green light source, red light source, and near infrared source respectively. D1, D2, D3, and D4 are detectors for detecting respective sources L1, L2, L3, and L4. LED=light-emitting diode, NIR=near-infrared.

The sensor can include optoelectronics for measuring the color and the flow rate of the wound fluid. Several arrangements of the optoelectronics are encompassed by the invention. For measuring color, light sources, e.g., a light emitting diode (LED) and a laser, can be mounted on one side of the sensor and a detector mounted on the opposite side of the sensor to detect light transmission through the fluid. See FIG. 3A. In a particular example, a blue light source, a green light source, and a red light source are all included, together with appropriate detectors, for determining color of the wound fluid. See FIGS. 3A and 3B. In another example, a white light source is used in conjunction with three detectors each having one of a red, blue, and green filter to determine color by transmission. See FIG. 3D. Color of the wound fluid can alternatively be determined by reflection, where the light sources and detectors are located on the same side of the detector. See FIGS. 3B and 3C.

Figure 3B:
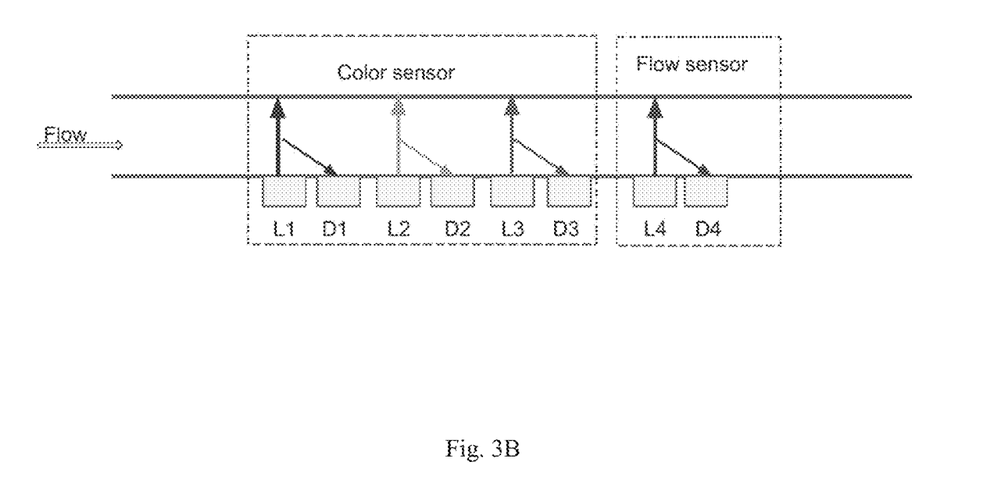
FIG. 3B diagrams the arrangement of color and flow sensors for detecting color and flow rate by reflection. Sources and detectors are defined as in FIG. 3A.
Figure 3C:
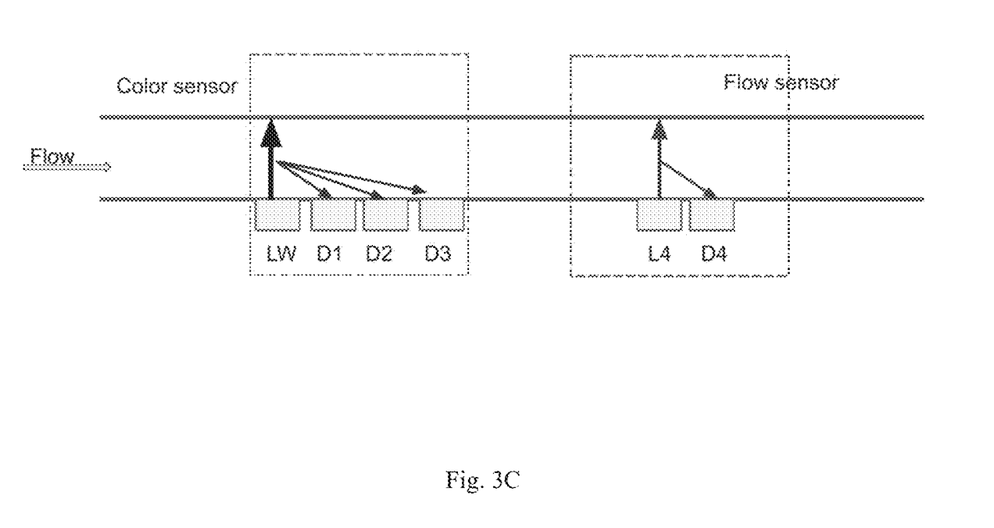
FIG. 3C diagrams an alternative arrangement of color and flow sensors for detecting color and flow rate by reflection. L4 and D4 are as described above. LW=white light source. D1, D2, and D3 are detectors with blue, green, and red filters, respectively.
Figure 3D:
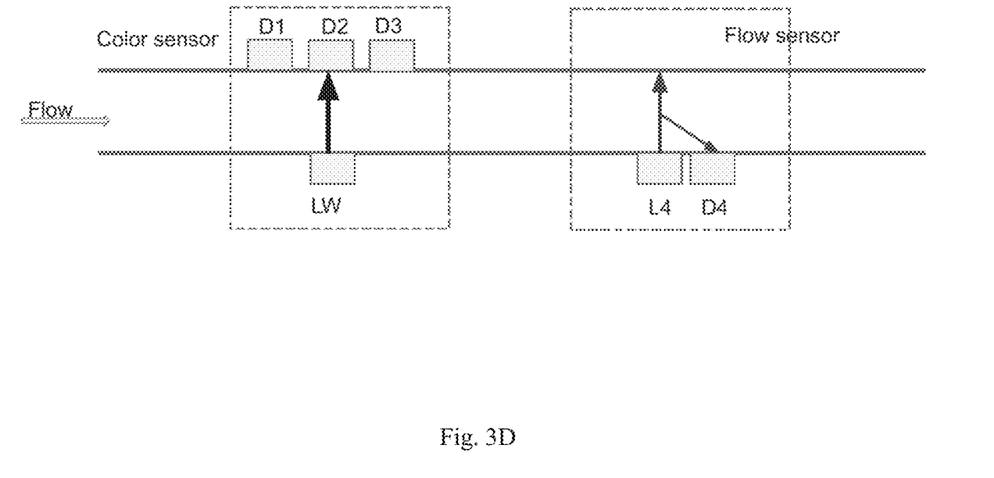
FIG. 3D diagrams the arrangement of color and flow sensors for detecting color by transmission and flow rate by reflection. LW, L4, D1, D2, D3, and D4 are defined above in the legend to FIG. 3C.

Turning to flow rate, it can be measured using a near-infrared laser (NIR) and detector by transmission (FIG. 3A) and by reflection (FIGS. 3B, 3C, 3D). Additional types of sensors are shown in FIGS. 4A-4E in which flow rate is detected by thermal flow, capacitive flow, acoustic flow, rotary flow, and piezo-resistive flow, respectively.

Figure 4A:
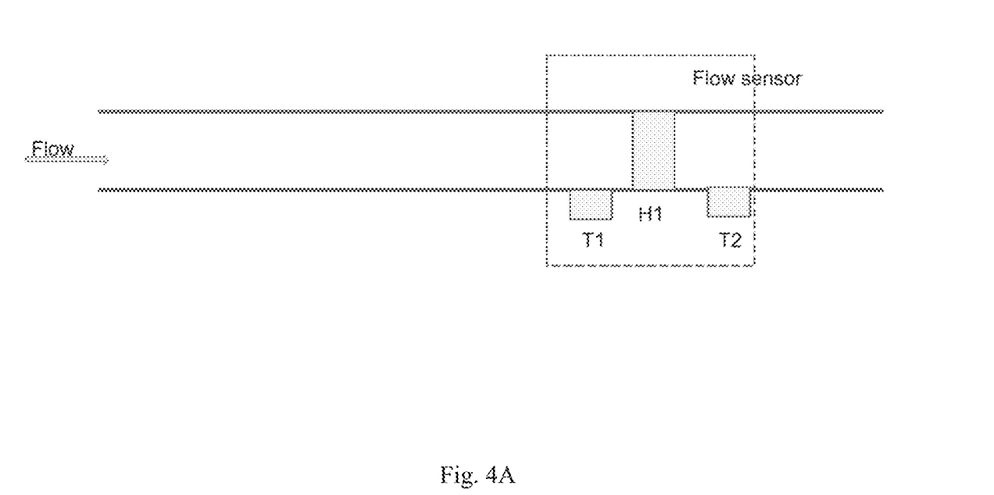
FIG. 4A is a diagram showing a flow sensor having an arrangement of temperature sensors and a heating element for determining flow rate by thermal flow. T1 and T2 are thermistors. H1 is a heating element.

Referring to FIG. 4A, thermistor T1 measures the temperature of a fluid flowing past before the fluid is heated by heating element H1, which heats the fluid to a specified temperature. Thermistor T2, located downstream of H1, detects the temperature of the fluid, which depends on the flow rate and initial temperature measured by T1. Alternatively, the amount of heat added by H1 is controlled such that the fluid temperature measured by T2 is constant. The amount of heat required to keep T2 constant is a measure of fluid flow.

Figure 4B:
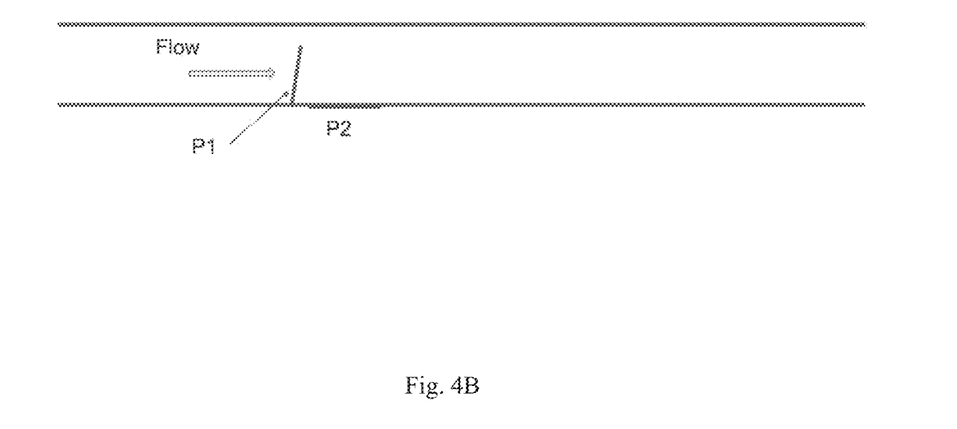
FIG. 4B is a diagram showing a flow sensor for determining flow rate by capacitive flow sensing. P1 and P2 are capacitor plates.

In FIG. 4B, fluid flow pushes plates P1 and P2 closer together, thereby changing the capacitance of the two plates base on the formula $C=K A/d$, where C is capacitance, K is the dielectric constant of the fluid, A is the area of P1 and P2, and d is the distance between P1 and P2.

Figure 4C:
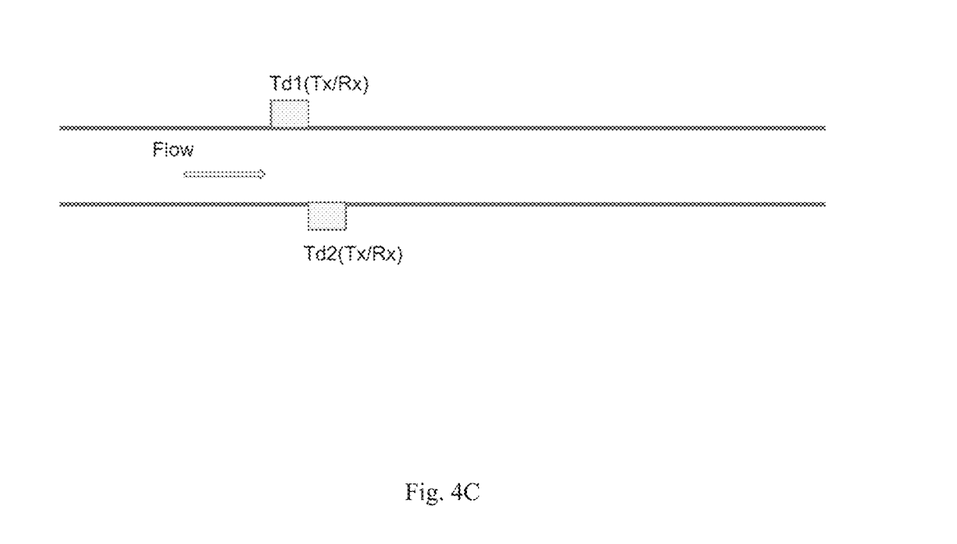
FIG. 4C is a diagram showing a flow sensor for determining flow rate by acoustic flow sensing. Td1 and Td2 are acoustic transducers both of which can transmit (Tx) and receive (Rx) ultrasound pulses.

Turning to FIG. 4C, an acoustic pulse is sent from Td1 and received by Td2 and from the elapsed time t, velocity, Vs1 is calculated. Similarly, using the time it takes for an acoustic pulse sent from Td2 to reach Td1, acoustic velocity Vs2 is calculated. For the direction of flow shown in FIG. 4C, $Vs1=Vs+Vf$, and $Vs2=Vs-Vf$, where Vs is the speed of sound in the fluid and Vf is the velocity of the fluid. Fluid velocity is $Vf=(Vs1-Vs2)/2$.

Figure 4D:
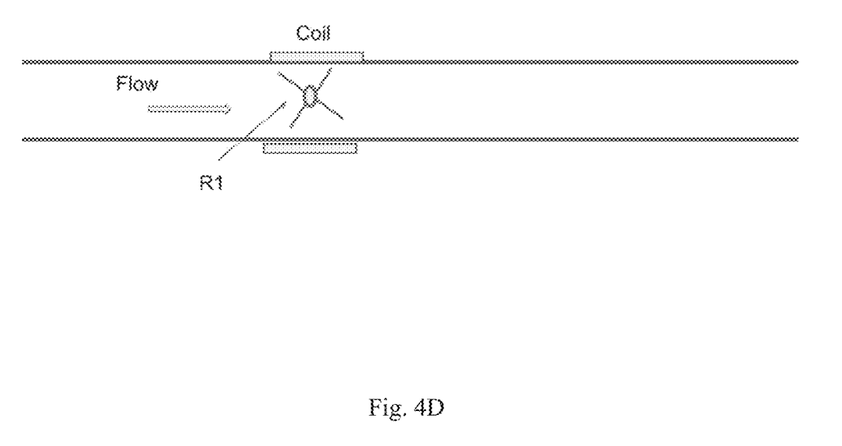
FIG. 4D is a diagram showing a flow sensor for determining flow rate with a rotary flow sensor. R1=rotor.

For rotary flow sensing, as shown in FIG. 4D, fluid flowing through the rotor causes it to spin. The rotational speed of the rotor depends on the flow speed of the fluid. Coils are used to magnetically detect the rotor rotational speed.

Figure 4E:
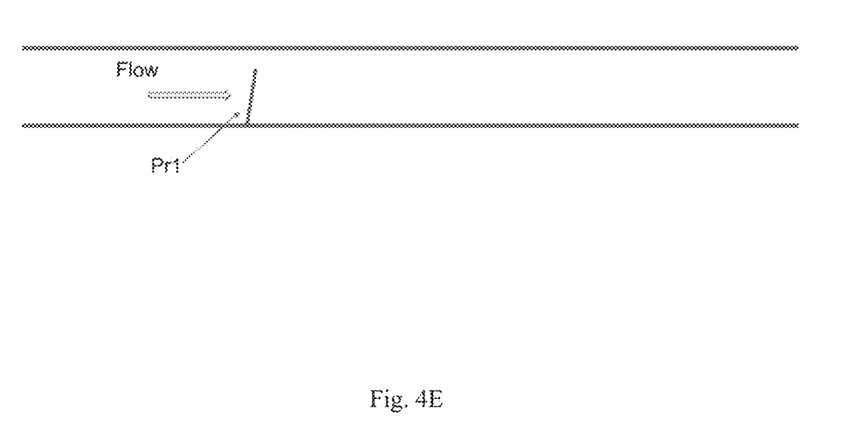
FIG. 4E is a diagram showing a flow sensor for determining flow rate with a piezo-resistive flow sensor. Pr1=piezo resistive membrane.

FIG. 4E shows piezoresistive flow sensing. The resistance of a piezo-resistive membrane (Pr1) is measured, which depends upon on the degree of bending of the membrane. The rate of fluid flow is proportional to the change in resistance of Pr1.

Further, flow can be determined by applying a heat pulse to the fluid with a laser and rapidly measuring heat dissipation in the fluid with a heat detector.

The sensor can include a combination of any of the color and flow determining modes described above. The sensor can detect a wide range of flow rates, from as low as 1 ml per day up to 75 ml per hour. Turning to color detection, the sensor is capable of differentiating between oxygenated blood (bright red), deoxygenated blood (dark red), infectious fluid (brownish), bile (greenish/yellow) and lymph fluid (clear). In particular systems, the sensor can also detect protein and/or pH.

As also mentioned above, the sensor includes a wireless transmitter for transmitting data for the color and the flow rate over one or more networks to the base station. The wireless transmitter can be, but is not limited to, near-field communication, Bluetooth, WiFi, 3G, 4G, 5G, and combinations of these modes.

The base station can be a stand-alone device or it can be a smartphone running an application. As set forth above, the base station receives data from the sensor, stores the data, e.g., in an EHR, and sends a notification over the one or more networks to a user device when certain predefined parameters are met. The notification is indicative of infection, bleeding, drainage disruption, or a combination of these conditions. In this way, a healthcare provider will receive the notification through the user device and take appropriate action.

The predefined parameters can include at least one of a high flow rate limit and a low flow rate limit, and the notification is sent if flow rate data associated with the flow rate falls above the high flow rate limit and/or if the flow rate data associated with the flow rate falls below the low flow rate limit. In a particular example, the predefined parameters include an expected flow rate and the notification is sent if the flow rate data differs by 50-100% (e.g., 50%, 60%, 70%, 80%, 90%, and 100%) from the expected flow rate.

In addition, or alternatively, the predefined parameters include a target color and the notification is sent if color data associated with the color of the fluid indicates that the color of the fluid is substantially equal to the target color. For example, if the target color is red and the color data indicates that the fluid is red, a notification is sent that the patient is bleeding. In another example, if the target color is brown and the color data indicates that the fluid is brown, a notification is sent that the patient has an infected wound. The predefined parameters can include more than one target color.

The wound monitoring system can incorporate predictive analytics such that predefined parameters discussed above can be refined and adjusted to obtain the best clinical outcomes. The predictive analytics can be performed, for example, by software in the base station using data stored therein.

In an example, when the parameters include an expected flow rate, the expected flow rate is adjustable based on a plurality of flow rate data stored in the base station. The base station in this example is configured to collect the plurality of flow rate data for a plurality of different patients and to generate one or more model that indicates expected healing rate over time. A particular model is generated based on the collected flow rate data taken together with one or more factors that include type of surgical procedure, gender, ethnicity, and comorbidity associated with one or more patients.

The base station can also be configured to select, based on information associated with a particular patient, a particular model and utilize the model to determine an expected drain output and/or healing time for the particular patient.

In another example, when the parameters include a target color, the base station can be configured to collect a plurality of color data from a plurality of different patients. With that data, one or more model is generated that indicate, for example, expected color change of wound fluid during wound healing over time. A particular model is generated based on one or more factors that include, but are not limited to, type of surgical procedure and patient condition.

Again, the base station can be configured to select, based on information associated with a particular patient, a particular model and utilize the model to determine the target color.

The base station can also be configured to generate models that incorporate both flow rate and target color, taking into account additional factors such as type of surgery, gender, ethnicity, comorbidity, and patient condition.

Flow rate and type of expected fluid, e.g., blood and interstitial fluid, determined from color data can be used to determine healing rate. For example, after surgery for a given procedure and patient characteristics mentioned above, a normal healing pattern includes blood flow (red color fluid) at a certain flow rate for the first few days following surgery and then bleeding slows and is replaced by increased amounts of interstitial fluid (clear liquid flow) at a certain flow rate. The expected color change combined with the expected flow rate can be used to predict patient healing time. This healing time model would be generated by the base station from data from multiple patients.

A second wound management system is also disclosed. Like the system described above, the second system includes a color/flow rate sensor, a base station, and a user device. Differently, in the second system, the base station receives data wirelessly over one or more networks from the sensor and transmits the data over one or more networks to a cloud server.

The cloud server can be configured in the same manner as that set forth above for the base station. More specifically, the cloud server is configured to receive data over one or more networks from the base station, to store the data in an EHR, and to send a notification over the one or more networks to a user device when certain predefined parameters are met. The notification is indicative of infection, bleeding, drainage disruption, or a combination of these conditions. The predefined parameters are discussed in detail, supra. In this way, a healthcare provider will receive the notification through the user device and take appropriate action.

In the second system, the predictive analytics described above are performed by software in the cloud server using data stored therein. Generation and selection of models based on the data is performed as set forth above.

Both of the above systems can be used with existing wound drain technologies, e.g., a Jackson-Pratt (JP) drain. In a JP drain, a flexible drainage tube is inserted into the patient and connected to a bulb where the fluids discharged by the body are collected. The sensor described above can be placed around the flexible tubing or the flexible tubing can be threaded through the sensor before it is connected to the bulb. See FIGS. 2A and 2B. Alternatively, the sensor can be provided with a short length of tubing that can be spliced into the JP drain drainage tube. The sensor is portable. For example, the sensor can be clipped to a belt or hung in a pouch around the waist of the patient.

The wound monitoring systems can be used in any situation in which a JP drain or similar drain is used. Examples include, but are not limited to, craniotomy, cancer surgery, plastic surgery, coronary artery bypass graft surgery, knee surgery, spinal surgery, bile duct surgery, liver surgery, pancreatic surgery, abscess surgery, and surgery to repair intestinal perforation.

Also provided is a method for monitoring a wound fluid using the systems described above. In a first step, a sensor is affixed to a wound drain tubing external to a patient. The sensor, described above, contains a color detector, a flow detector, and a wireless transmitter for transmitting data for the color and the flow rate over one or more networks to a base station. Detection modes and wireless modes are those set forth at page 6, line 18 through page 7, line 16, supra.

In a second step, the base station is programmed with parameters for notification related to the data for the color and the flow rate. The base station has all of the functionality described above.

Next, the base station is activated such that the base station periodically updates an EHR of the patient with the data for the color and the flow rate and continuously compares the data with the parameters. When the parameters are met, the notification indicating one or more of infection, bleeding, and drain blockage is sent to a user device over one or more networks. The parameters and notifications have been described in detail above.

Finally, the notification sent to the user device prompts the caregiver to provide proper medical attention.

Figure 5:
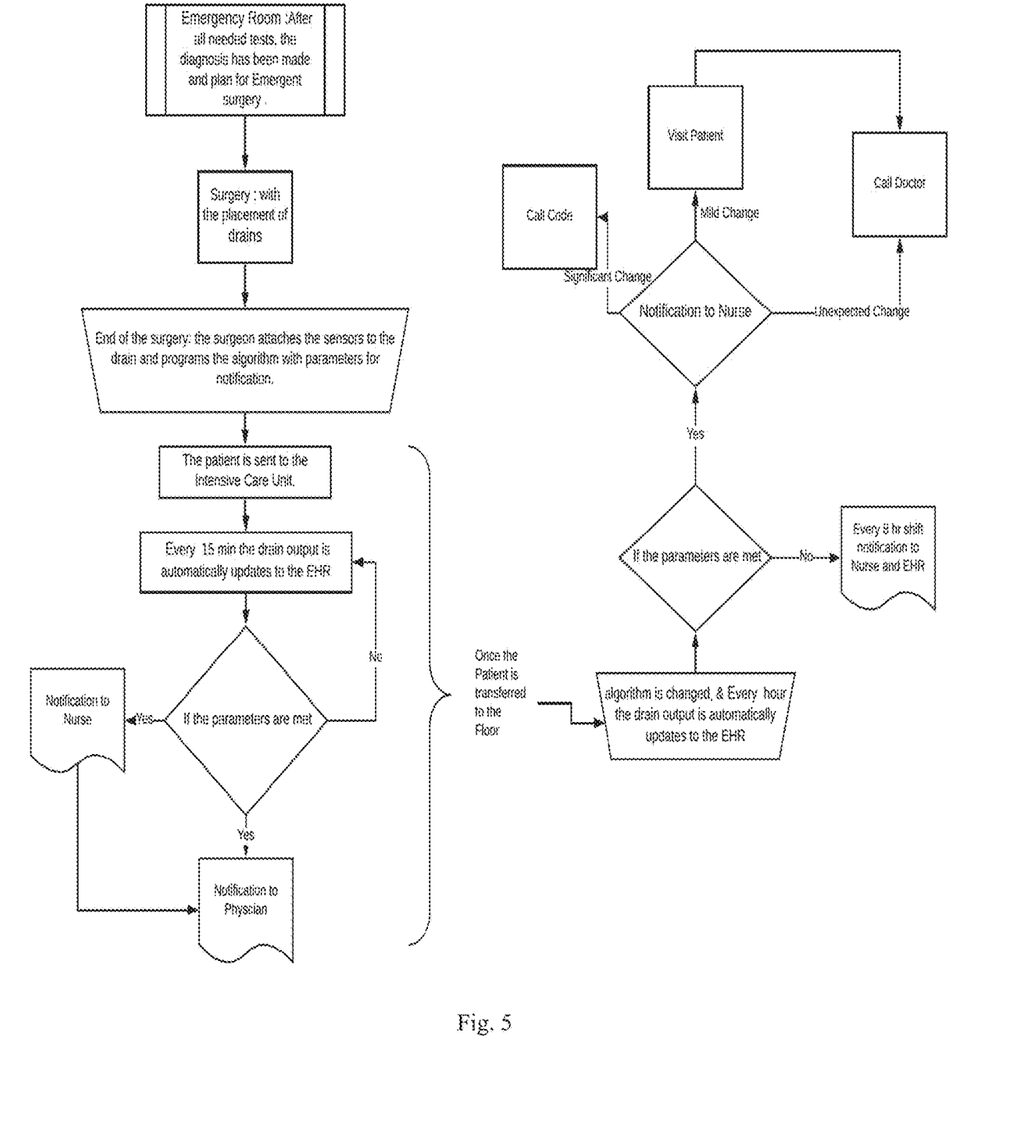
FIG. 5 is a flow chart showing a method of using a wound monitoring system in a hospital setting.
Figure 6:
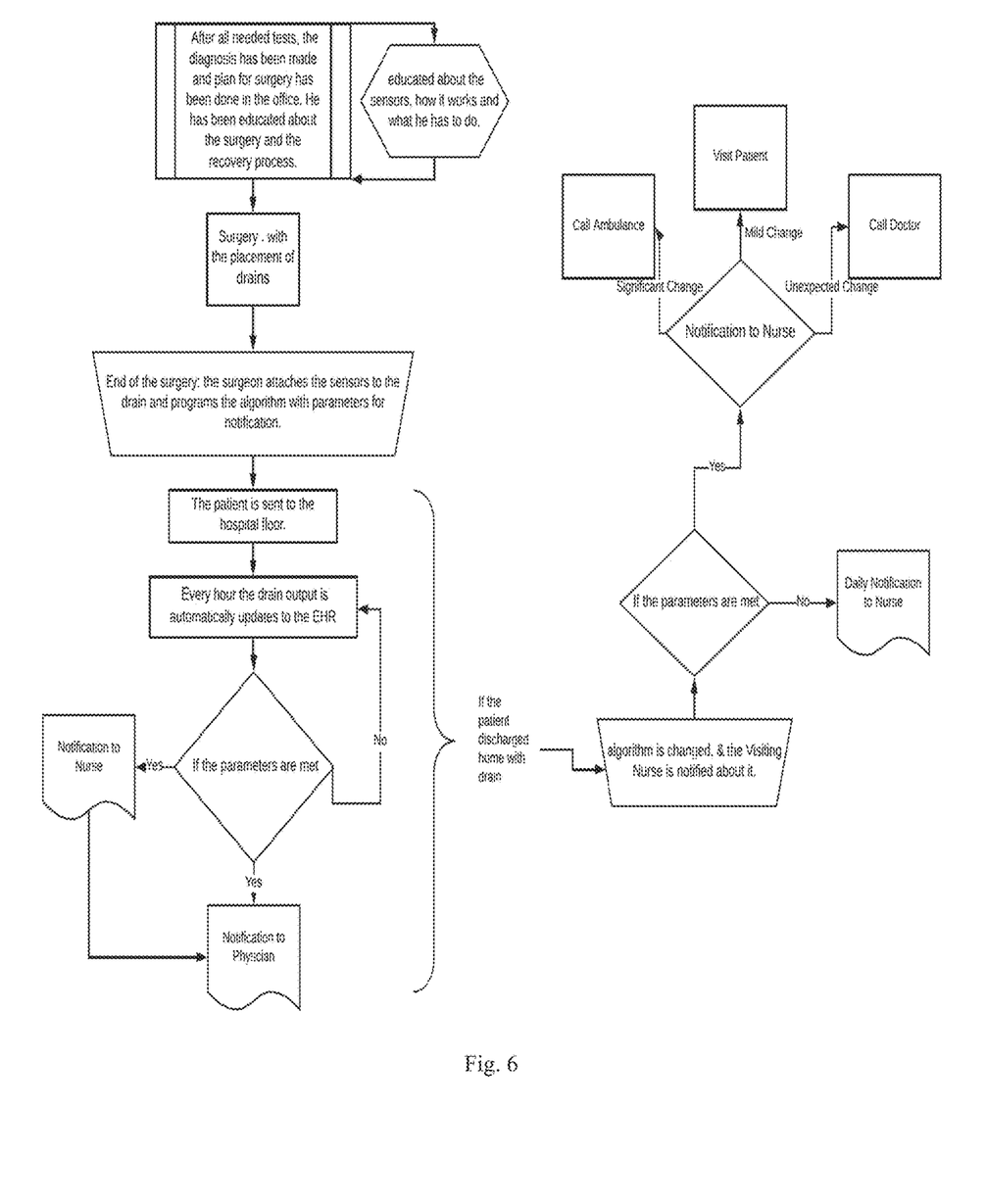
FIG. 6 is a flow chart showing a method of using a wound monitoring system in a hospital setting and after discharge to a residential setting.
Figure 7A:
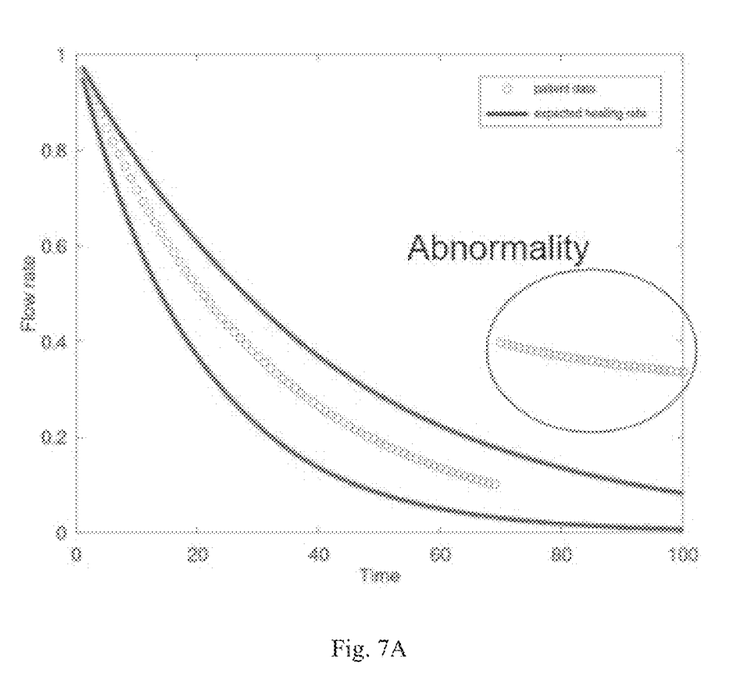
FIG. 7A is a graph of flow rate of wound drain fluid versus time, showing upper and lower boundaries of flow rates expected during healing (dark lines) and measured flow rates (circles). Measured flow rates outside the upper and lower boundaries are shown, indicating abnormal wound healing.
Figure 7B:
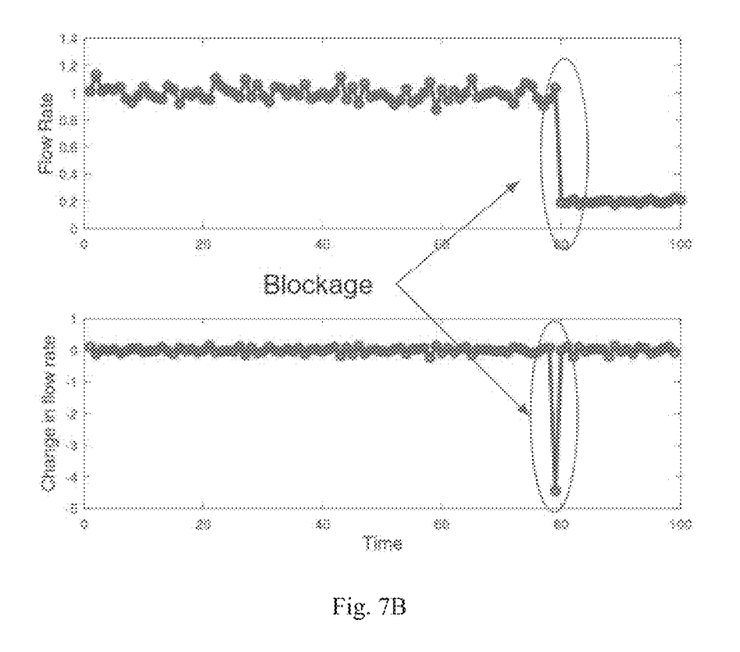
FIG. 7B shows graphs of flow rate of wound drain fluid versus time (upper graph) and change in flow rate versus time (lower graph). A sudden change in flow rate is shown, indicating blockage of the wound drain.

The wound fluid monitoring method can be carried out in a hospital setting, in a home setting, and in both settings. The method is shown schematically in FIGS. 5 and 6.

For example, in a hospital setting, the method can be employed in the recovery area or intensive care unit shortly after insertion of a wound drain during surgery. See FIG. 5, left side. When the patient is sufficiently recovered to be moved to a hospital room, the notification parameters are adjusted accordingly. See FIG. 5, right side.

In another example, the wound monitoring method is carried out in both the hospital setting and the home setting. See FIG. 6. The method used in the hospital setting is described above. When the patient is discharged, the parameters are adjusted accordingly. See FIG. 6, right side. Advantageously, when the method is practiced in a home setting, the method employs the second wound monitoring system described above having a cloud server.

By continually monitoring wound drain fluid color and flow rate automatically according to the one or more embodiments described herein, the volume of wound fluid and color does not have to be subjectively monitored by, for example, an attending physician or nurse. Advantageously, the one or more embodiments described herein facilitate early detection of complications during post-operative recovery, which in turn assists the patient in healing, monitoring the patient's recovery, and avoiding complications. Therefore, the one or more embodiments described herein provide an improvement in the existing technology field of wound drainage systems.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

EXAMPLES

Example 1

Outpatient Case Scenario

A 75-year-old male is diagnosed with pancreatic cancer. He looks for the best hospital and surgeon with the goal of having the fewest complications and the shortest hospital stay.

After completion of pre-surgical workup, he undergoes robotic assisted surgery. Four days after the surgery he is discharged home with an abdominal wound drain in place. He is asked by his healthcare provider to monitor the wound drain fluid color and volume output. In the next few days at home he empties the drain but fails to document the drain output. He has only a rough estimate of how much he empties every day.

His wife calls the doctor saying that he is very lethargic today and has fever. The doctor asks her to bring him to the emergency room (ER). The ER personnel ask him what the drain output has been and whether the wound fluid volume has been going up or down, he is unable to answer accurately. It is determined that he is septic as a result of a large fluid collection in the abdomen which has formed an abscess.

If the drain output had been monitored more accurately, the reduced fluid output would have been noticed as indicative of a drain obstruction and pooling of the fluid in the abdomen.

Example 2

Outpatient Case Scenario with Wound Drain Management System of the Invention

The patient discussed above in Example 1 is educated by his caregivers regarding the surgery and the recovery process. The education includes a discussion of the operation of the wound fluid monitor system and any actions he will need to take.

Following surgery and wound drain placement, the surgeon attaches the sensors to the drain and programs the base station with appropriate notification parameters.

After post-operative recovery, the patient is sent to the hospital floor. The wound management system continuously monitors the wound drain output and automatically updates the patients EHR every hour. If the notification parameters are met, the system sends a notification to one or more user devices belonging to the responsible nurse and/or physician.

The patient is ready to be discharged from the hospital with the drain still in place. The notification parameters are changed in the base station such that a daily drain report is sent to a user device of a visiting nurse. Additionally, notification parameters are also changed to account for expected changes in flow rate and fluid color, e.g., based on the number of days in the hospital before discharge and the type of surgery.

If parameters are met, a notification is sent to the user device of the visiting nurse and at the doctor's office. Depending upon what parameters are met, the visiting nurse visits the patient or recommend that the patient go to the doctor's office or hospital.

Example 3

Inpatient Case Scenario

A 60-year-old female arrives at the hospital complaining of abdominal pain. Examination of the patient reveals sepsis resulting from an intestinal perforation. She undergoes emergency laparotomy to remove pus and feces from the abdominal cavity.

The surgeon performs an intestinal resection and anastomosis. A wound drain is inserted at the anastomosis site so that, in the event that a leak developed, it is readily detected.

The patient gradually improves and her wound drain collects the expected pink-colored serosanguinous fluid. The fluid output gradually decreases and the patient has minimal discomfort on initiation of a liquid diet. On the following day, she has a fever but, as she was hungry, she continues to drink more. When trying solid food, she experiences significant abdominal pain. Her nurse notifies the attending physician.

Upon examination, the patient is again found to be septic with high fever and low blood pressure.

She is returned to surgery, where the surgeon notices that the wound drain has a dark green to brown hue to it. Hospital staff does not know at what time the fluid color change occurred.

Example 4

Inpatient Case Scenario with Wound Drain Monitoring System of the Invention

After the patient described in Example 3 undergoes surgery, the surgeon attaches the sensors to the drain and programs the base station with appropriate notification parameters and sends the patient to the intensive care unit. The wound management system continuously monitors the wound drain output and automatically updates the patients EHR every hour. If the notification parameters are met, the system sends a notification to one or more user devices in the possession of the responsible nurse and/or physician.

When sufficiently recovered, the patient is moved to the hospital floor. The responsible nurse or physician modifies the notification parameters such that notifications are sent to the user device of the caregivers, e.g., the responsible nurse and the attending physician.

Typically, changes in wound drain volume and color is recorded once per shift, i.e., once every 12 hours. The wound drain management system of the invention continuously monitors these properties. In the case of this patient, the system detects subtle color changes in her wound drain fluid and does so earlier than manual monitoring.

The system sends a notification to the user device of the nurse, who examines the patient and calls the attending physician, if necessary. In this case, the color change is indicative of a leak in the anastomosis. Feeding is halted and additional tests ordered to determine if a second surgery is warranted.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A wound monitoring system, comprising:
a sensor for detecting color and flow rate of a fluid flowing through a wound drain tubing, the sensor including a wireless transmitter for transmitting data for the color and the flow rate over one or more networks to a base station;
the base station for receiving the data over the one or more networks and the base station for storing the data, the base station including at least one processor configured to:
compare the data with predefined parameters stored at the base station, send a notification over the one or more networks to a user device if the predefined parameters are met by the data, and update an electronic health record (EHR) with the data; and
the user device for receiving the notification over the one or more networks and for modifying the predefined parameters stored at the base station, the user device configured to present the notification on a display device of the user device to a user, to accept one or more input commands via a graphical user interface of the user device from the user for modifying the predefined parameters, and to transmit the modified predefined parameters to the base station over the one or more networks, wherein the at least one processor of the base station is further configured to analyze the EHR and the data stored at the base station to predict clinical outcomes and to modify the predefined parameters based on the predicted clinical outcomes.

2. The wound monitoring system of claim 1, wherein the sensor further includes optoelectronics for measuring the color and the flow rate of the fluid.

3. The wound monitoring system of claim 1, wherein the sensor further includes a laser for applying a heat pulse to the fluid and a heat detector for rapidly measuring heat dissipation in the fluid.

4. The wound monitoring system of claim 1, wherein the predefined parameters include at least one of a high flow rate limit and a low flow rate limit, and the notification is sent if flow rate data associated with the flow rate falls above the high flow rate limit when the predefined parameters include the high flow rate limit or the flow rate data associated with the flow rate falls below the low flow rate limit when the predefined parameters include the low flow rate limit.

5. The wound monitoring system of claim 1, wherein the predefined parameters include an expected flow rate and the notification is sent if the flow rate data differs by 50-100% from the expected flow rate.

6. The wound monitoring system of claim 5, wherein the expected flow rate is adjustable based on a plurality of flow rate data stored in the base station.

7. The wound monitoring system of claim 6, wherein the base station is configured to collect the plurality of flow rate data for a plurality of different patients and generate one or more models that indicate expected healing rate over time, wherein a particular model is generated based on the collected flow rate data and one or more factors that include a surgical procedure, gender, ethnicity, and comorbidity associated with one or more patients.

8. The wound monitoring system of claim 7, wherein the at least one processor of the base station is further configured to select, based on information associated with a particular patient, a particular model of the one or more models and utilize the model to determine at least one of an expected drain output and healing time for the particular patient.

9. The wound monitoring system of claim 1, wherein the predefined parameters include a target color and the notification is sent if color data associated with the color of the fluid indicates that the color of the fluid is substantially equal to the target color.

10. The wound monitoring system of claim 9, wherein the base station is configured to collect a plurality of color data for a plurality of different patients and generate one or more model, wherein a particular model is generated based on one or more factors that include one or more of a surgical procedure and patient conditions.

11. The wound monitoring system of claim 10, wherein the at least one processor of the base station is further configured to select, based on information associated with a particular patient, a particular model of the one or more models and utilize the model to determine the target color.

12. The wound monitoring system of claim 1, wherein the notification is indicative of infection, bleeding, drainage disruption, or a combination thereof.

13. A wound monitoring system, comprising:
a sensor for detecting color and flow rate of a fluid flowing through a wound drain tubing, the sensor including a wireless transmitter for transmitting data for the color and the flow rate;
a base station for receiving the data and transmitting the data over one or more networks to a cloud server, the cloud server including at least one processor configured to:
compare the data with predefined parameters stored at the cloud server,
send a notification over the one or more networks if the predefined parameters are met by the data, and
update an electronic health record (EHR) with the data; and
a user device for receiving the notification over the one or more networks and for modifying the predefined parameters stored at the cloud server, the user device configured to present the notification on a display device of the user device to a user, to accept one or more input commands via a graphical user interface of the user device from the user for modifying the predefined parameters, and to transmit the modified predefined parameters to the cloud server over the one or more networks,
wherein the at least one processor is further configured to analyze the EHR and the data stored at the cloud server to predict clinical outcomes and to modify the predefined parameters based on the predicted clinical outcomes.

14. The wound monitoring system of claim 13, wherein the sensor further includes optoelectronics for measuring the color and the flow rate of the fluid.

15. The wound monitoring system of claim 13, wherein the sensor further includes a laser for applying a heat pulse to the fluid and a heat detector for rapidly measuring heat dissipation in the fluid.

16. The wound monitoring system of claim 13, wherein the predefined parameters include at least one of a high flow rate limit and a low flow rate limit, and the notification is sent if flow rate data associated with the flow rate falls above the high flow rate limit when the predefined parameters include the high flow rate limit or the flow rate data associated with the flow rate falls below the low flow rate limit when the predefined parameters include the low flow rate limit.

17. The wound monitoring system of claim 13, wherein the predefined parameters include an expected flow rate and the notification is sent if the flow rate data differs by 50-100% from the expected flow rate.

18. The wound monitoring system of claim 17, wherein the expected flow rate is adjustable based on a plurality of flow rate data stored in the cloud server.

19. The wound monitoring system of claim 13, wherein the predefined parameters include a target color and the notification is sent if color data associated with the color of the fluid indicates that the color of the fluid is substantially equal to the target color.

20. The wound monitoring system of claim 13, wherein the notification is indicative of infection, bleeding, drainage disruption, or a combination thereof.

21. A method for monitoring a wound fluid, comprising:
affixing a sensor to a wound drain tubing external to a patient, the sensor containing a color detector, a flow detector, and a wireless transmitter for transmitting data for the color and the flow rate over one or more networks to a base station;
programming the base station with parameters for notification related to the data for the color and the flow rate, the notification to be sent to a user device over the one or more networks when the data for the color and the flow rate data meet the parameters indicating one or more of infection, bleeding, and drain blockage;
activating the base station, wherein the activating causes the base station to periodically update an electronic health record of the patient with the data for the color and the flow rate and continuously compare the data with the parameters,
wherein, when the parameters are met, the notification is sent to the user device over the one or more networks such that proper medical attention can be provided.

22. The method of claim 21, wherein the parameters include at least one of a high flow rate limit and a low flow rate limit, and the base station is programmed to send the notification if flow rate data associated with the flow rate falls above the high flow rate limit when the parameters include the high flow rate limit or the flow rate data associated with the flow rate falls below the low flow rate limit when the parameters include the low flow rate limit.

23. The method of claim 21, wherein the parameters include an expected flow rate and the base station is programmed to send the notification if the flow rate data differs by 50-100% from the expected flow rate.

24. The method of claim 21, wherein the parameters include a target color and the base station is programmed to send the notification if color data associated with the color of the fluid indicates that the color of the fluid is substantially equal to the target color.

25. The method of claim 21, wherein the notification is indicative of infection, bleeding, drainage disruption, or a combination thereof.

* * * * *